(12) United States Patent
Ward

(10) Patent No.: US 7,294,145 B2
(45) Date of Patent: Nov. 13, 2007

(54) STENT WITH DIFFERENTLY COATED INSIDE AND OUTSIDE SURFACES

(75) Inventor: Liam Ward, Co Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 169 days.

(21) Appl. No.: 10/786,022

(22) Filed: Feb. 26, 2004

(65) Prior Publication Data

US 2005/0192662 A1  Sep. 1, 2005

(51) Int. Cl.
*A61F 2/06* (2006.01)

(52) U.S. Cl. ............ 623/1.11; 623/1.16; 623/1.42

(58) Field of Classification Search .......... 623/1.15, 623/1.16, 1.22, 1.11, 1.12, 1.13, 1.14, 1.42, 623/1.43
See application file for complete search history.

(56) References Cited

U.S. PATENT DOCUMENTS

| | | | | |
|---|---|---|---|---|
| 5,064,435 A | * | 11/1991 | Porter | 623/23.7 |
| 5,330,500 A | * | 7/1994 | Song | 623/1.2 |
| 6,249,952 B1 | * | 6/2001 | Ding | 29/460 |
| 6,428,569 B1 | * | 8/2002 | Brown | 623/1.15 |
| 6,544,544 B2 | * | 4/2003 | Hunter et al. | 424/424 |
| 6,793,672 B2 | * | 9/2004 | Khosravi et al. | 623/1.13 |
| RE38,653 E | * | 11/2004 | Igaki et al. | 606/198 |
| 7,105,018 B1 | * | 9/2006 | Yip et al. | 623/1.15 |
| 2002/0138132 A1 | | 9/2002 | Brown | |
| 2003/0204245 A1 | | 10/2003 | Brightbill | |
| 2004/0093076 A1 | * | 5/2004 | White et al. | 623/1.16 |

FOREIGN PATENT DOCUMENTS

WO   WO 2004/021929 A1   3/2004

* cited by examiner

*Primary Examiner*—Thomas J. Sweet
(74) *Attorney, Agent, or Firm*—Kenyon & Kenyon LLP

(57) ABSTRACT

A medical device, e.g., a stent, is provided with different coatings on different surfaces, or with a coating on only one of the inside or outside surface. In accordance with certain embodiments, two different stent members are provided, one to fit inside of the other. When the two stent members are separate, both stent members are coated, each with a different composition, or only one stent member is coated. Then, one stent member is placed inside the other to form the final stent. The resulting stent has one composition on its outside surface and a different composition on its inside surface, or coating only on either the inside or outside surface.

8 Claims, 4 Drawing Sheets

STENT WITH DIFFERENTLY COATED INSIDE AND OUTSIDE SURFACES

FIELD OF THE INVENTION

The present invention is directed to the field of applying therapeutic and protective coatings to tubular medical devices, such as stents.

BACKGROUND

Medical implants are used for innumerable medical purposes, including the reinforcement of recently re-enlarged lumens, the replacement of ruptured vessels, and the treatment of disease such as vascular disease by local pharmacotherapy, i.e., delivering therapeutic drug doses to target tissues while minimizing systemic side effects. Such localized delivery of therapeutic agents has been proposed or achieved using medical implants which both support a lumen within a patient's body and place appropriate coatings containing absorbable therapeutic agents at the implant location. Examples of such medical devices include stents, stent grafts, vascular grafts, catheters, guide wires, balloons, filters (e.g., vena cava filters), intraluminal paving systems, implants and other devices used in connection with drug-loaded polymer coatings. Such medical devices are implanted or otherwise utilized in body lumina and organs such as the coronary vasculature, esophagus, trachea, colon, biliary tract, urinary tract, prostate, brain, and the like.

The delivery of stents is a specific example of a medical procedure that may involve the deployment of coated implants. Stents are tube-like medical devices designed to be placed within the inner walls of a lumen within the body of a patient. The tube walls of the stents are typically patterned, leaving openings, with the material of the stent forming a scaffold for the lumen wall. Stents are made, for example, of stainless steel, Tantalum, Platinum or Nitinol alloys. The stents are maneuvered to a desired location within a lumen of the patient's body, and then typically expanded to provide internal support for the lumen. Stents may be self-expanding or, alternatively, may require external forces to expand them, such as by inflating a balloon attached to the distal end of the stent delivery catheter.

The mechanical process of applying a coating onto a stent may be accomplished in a variety of ways, including, for example, spraying the coating substance onto the stent, so-called spin-dipping, i.e., dipping a spinning stent into a coating solution to achieve the desired coating, and electro-hydrodynamic fluid deposition, i.e., applying an electrical potential difference between a coating fluid and a target to cause the coating fluid to be discharged from the dispensing point and drawn toward the target. In these prior stent coating systems, the stents typically are coated on all surfaces. For example, with a coating spray application system, the relatively open patterned structure of the stent permits a coating spray to pass through the open areas and coat the inner surfaces of the stent. Similarly, with a spin-dipping stent coating system, all the surfaces of the stent, interior and exterior, are exposed to the coating fluid upon immersion into the coating bath.

In the typical stent deployment, the outside surface of the stent contacts the vessel wall. The inside surface of the stent is exposed to the fluid, e.g., blood, passing through the lumen.

SUMMARY OF THE INVENTION

In some instances, it may be desired that the coating on the outside surface of the stent that contacts the vessel wall is different from the coating on the inside of the stent. For example, it may be desirable to treat the vessel wall and bloodstream with different therapeutic agents.

Alternatively, in some instances, it may be desired that the outside surface of the stent is coated while the inside surface of the stent is not coated. For example, it may be desired that there be no coating on the inside of the stent in order to avoid significant exposure of the coating material to the bloodstream and/or to minimize the risk of slippage of the stent on the delivery device.

Alternatively, in some instances, it may be desired that the inside surface of the stent is coated while the outside surface of the stent is not coated. For example, it may be desired that a therapeutic agent be exposed only to the internal lumen or bloodstream and not significantly to the vessel wall.

In certain embodiments, the present invention is directed to a method and system for providing a medical device with different coatings on different surfaces of the medical device. The medical device may be, for example, a stent. In accordance with certain embodiments, two different stent members are provided, one to fit inside of the other. When the two stent members are separate, each stent member is coated, each with a different composition. Then, one stent member is placed inside the other to form the final stent. The resulting stent has one coating composition on its outside surface and a different coating composition on its inside surface.

In certain embodiments, the present invention is directed to a method and system for providing a medical device with coating only on one of the inside or outside surface of the medical device. The medical device may be, for example, a stent. In accordance with certain embodiments, two different stent members are provided, one to fit inside of the other. When the two stent members are separate, only one of the stent members is coated, depending on whether it is desired to have coating on the inside surface or outside surface of the final stent. Then, one stent member is placed inside the other to form the final stent. The resulting stent has a coating only on either its outside surface or its inside surface.

The foregoing method and system is amenable to a number of variations. Variations will be appreciated by persons of skill in the art in view of this disclosure.

BRIEF DESCRIPTION OF THE DRAWINGS

The foregoing and further objects, features and advantages of the invention will become apparent from the following description of preferred embodiments with reference to the accompanying drawings, wherein like numerals are used to represent like elements and wherein.

DETAILED DESCRIPTION

Figure 1:
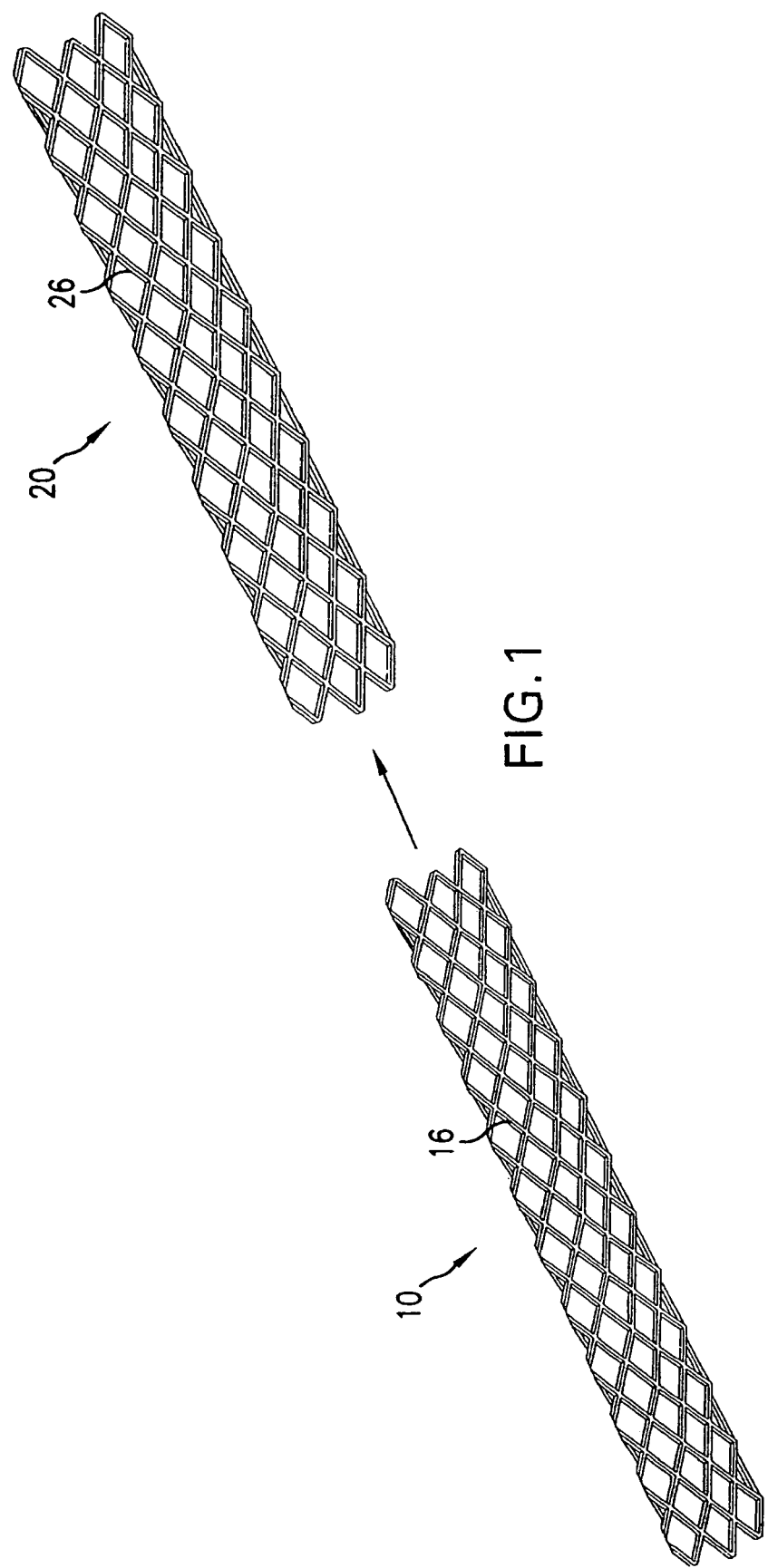
FIG. 1 shows a perspective view of two stent members prior to being assembled together.
Figure 4:
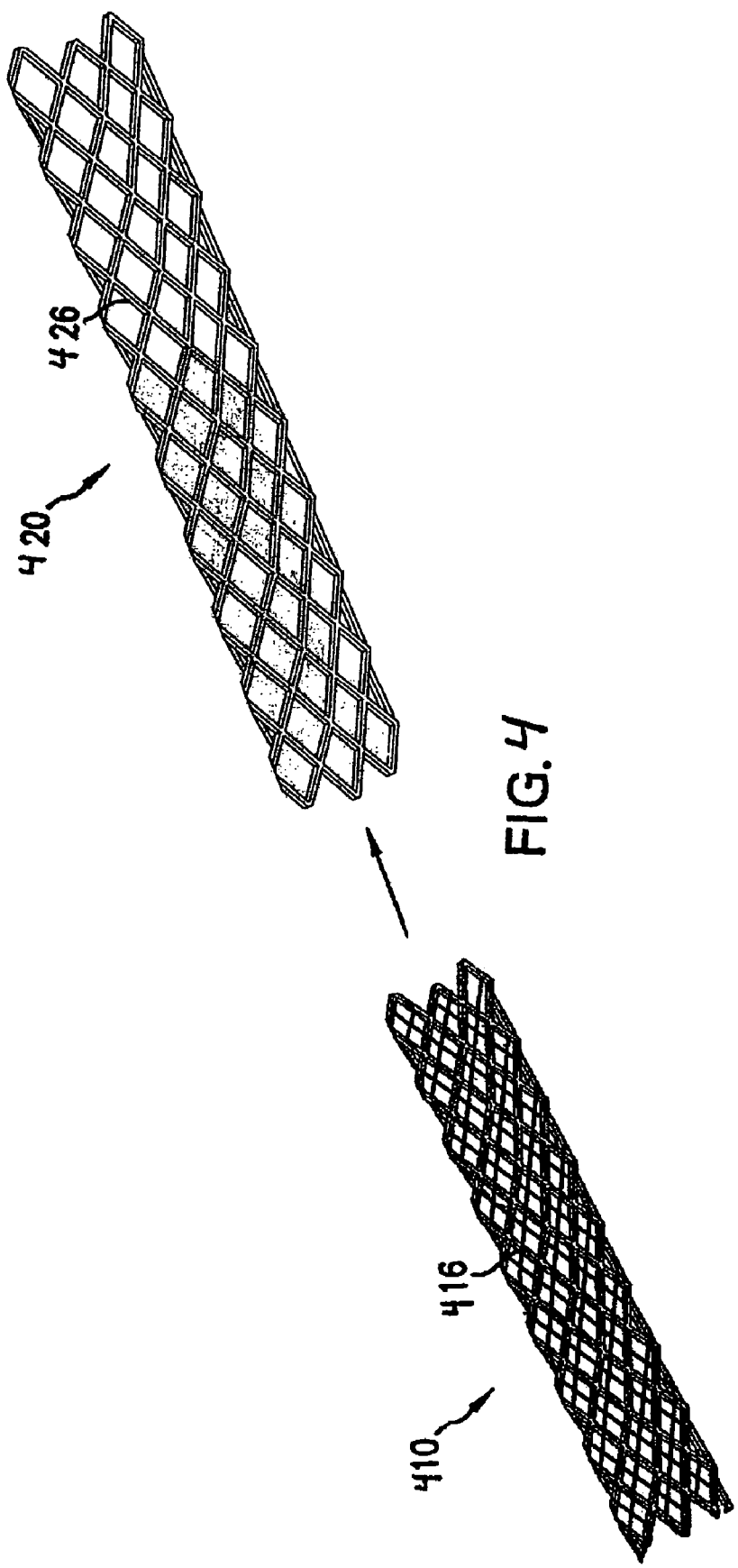
FIG. 4 shows another perspective view of two stents prior to being assembled together.

FIG. 1 illustrates a first stent member 10 and a second stent member 20. Each stent member 10, 20 may have any of a number of suitable geometries and characteristics. For example, each stent member 10, 20 may have a geometry similar to any of a number of stent designs known in the art, or variations thereof. The geometry is typically that of a patterned structure formed in a generally tubular shape, as shown generically in FIG. 1. The patterned structure of stent member 10 may be generally the same as the patterned structure of stent member 20. Alternatively, the patterned structure of stent member 10 may be different from the patterned structure of stent member 20. For example, in FIG. 4 stent member 410 may be comprised of a different patterned structure of stent parts 416 than the patterned structure of stent parts 426 of stent member 420. In the embodiment illustrated in FIG. 1, the patterned structure of stent member 10 is similar to the patterned structure of stent member 20, in that the stent parts 16 of stent member 10 are similar to the stent parts 26 of stent member 20. If desired, one stent member may have more stent parts than the other. Also as seen in FIG. 4. one stent member may be longer than the other.

The stent members 10, 20 may be expandable in accordance with conventional expansion mechanisms. For example, they may be balloon 110 expandable or self-expandable. The stent members 10, 20 may be made of suitable stainless steel, tantalum, platinum, or nitinol alloys.

The stent members 10, 20 are to receive a coating, for example a coating of a therapeutic material. The coating of the stent members 10, 20 may be accomplished in any of a number of ways. For example, the stent members 10, 20 may be coated using any of a number of coating methods known in the art, or variations thereof.

Depending on the desired configuration, either or both of stent members 10, 20 may be coated, and each may be coated with a different coating. Then, the stent members 10, 20 are assembled together. Stent member 10 is designed to fit inside stent member 20. As shown by the arrow in FIG. 1, stent member 10 is inserted longitudinally into the internal space defined by stent member 20.

Figure 2:
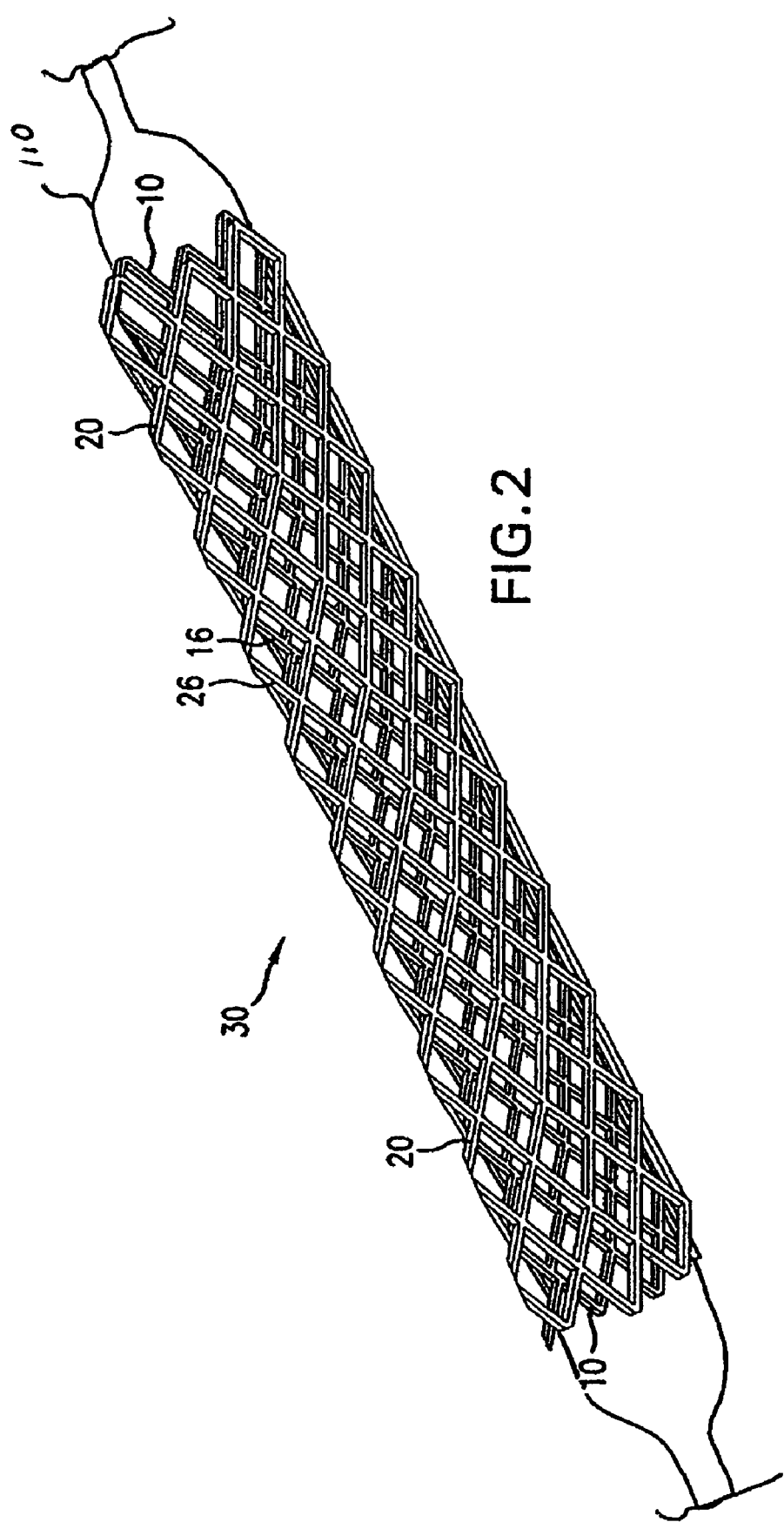
FIG. 2 shows a perspective view of a stent assembly in accordance with one embodiment of the invention, made from the assembly of the two stents shown in FIG. 1 and a delivery device.

FIG. 2 shows a stent 30 formed by the two stent members 10, 20. After stent member 10 is placed inside of stent member 20, the two may be affixed, bonded or mechanically joined together, if desired. For example, the stent members 10, 20 may be welded at various points or joined by a suitable adhesive.

In the assembled embodiment shown in FIG. 2, stent parts 26 of stent member 20 lie directly over stent parts 16 of stent member 10. Thus the assembled stent has a number of adjacent, paired parts (e.g., parts 16, 26). The illustration shows the inner stent member 10 slightly shifted in order that its parts are visible in the drawing (for clarity in this description). It will be appreciated that the stent parts 16, 26 may be entirely overlapping when the stent 30 is assembled, such that stent parts 16 are not easily visible from outside the stent.

Figure 3:
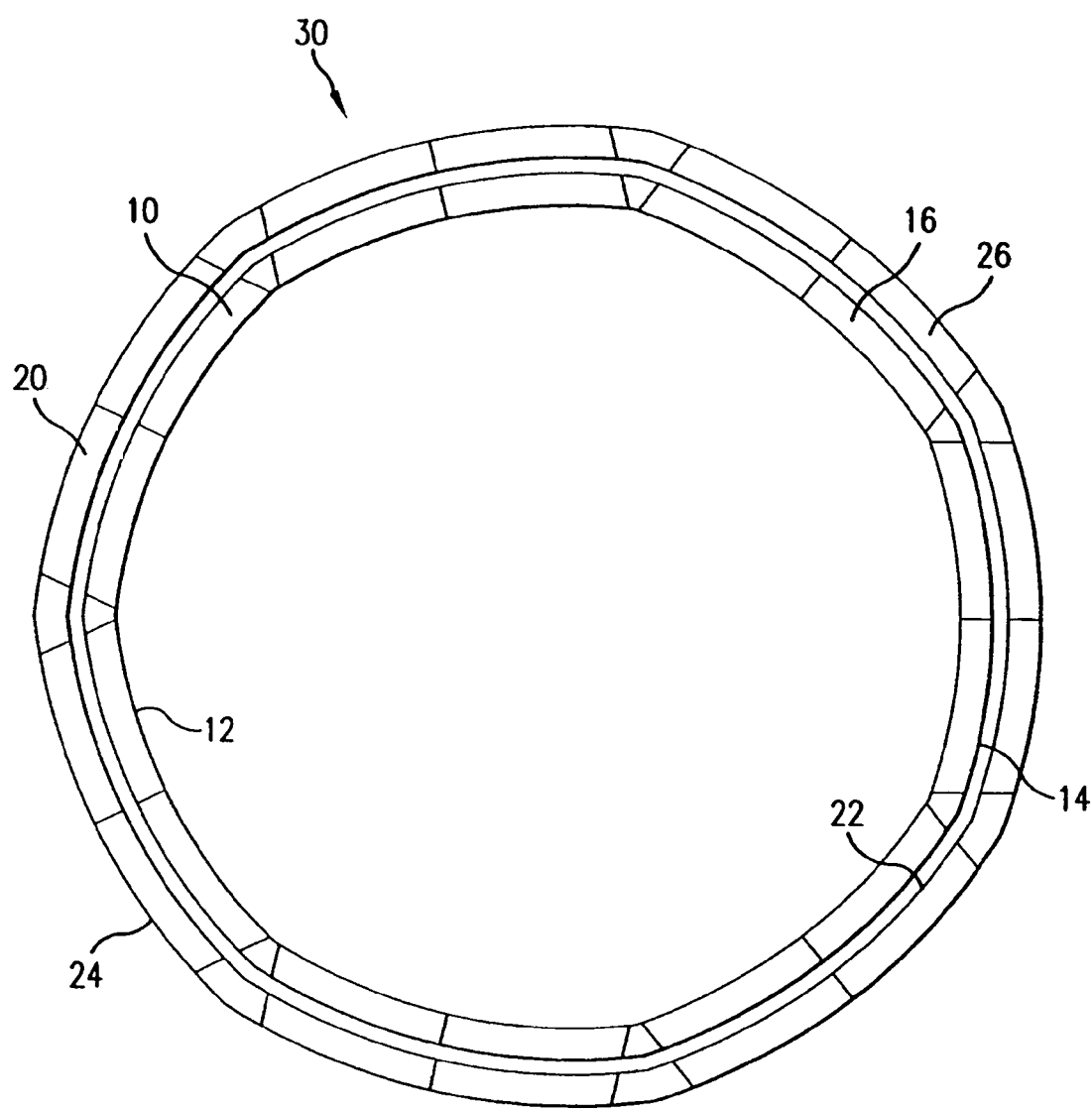
FIG. 3 illustrates an end view of the stent of FIG. 2.

FIG. 3 shows an end view of the stent 30. It should be appreciated that in many embodiments there will be no gap between stent member 10 and stent member 20 once assembled, but FIG. 3 shows a gap between the two (again, for clarity in this description). As can be seen in FIG. 3, the inside surface 12 of stent member 10 forms the inside surface of stent 30, and the outside surface 24 of stent member 20 forms the outside surface of stent 30.

The resulting stent 30 has differences in coatings between the inside surface 12 and the outside surface 24. For example, the inside surface 12 and the outside surface 24 may be coated with different materials or therapeutic agents. Alternatively, only one of the inside surface 12 and the outside surface 24 may be coated.

It will be appreciated that a stent in accordance with embodiments of the invention has numerous advantages. For example, the stent 30 may release two different therapeutic agents simultaneously or at different times, depending on the properties of the coatings used.

Differences in the geometries of the first and second stent members may be chosen for particular uses. For example, one stent member may be longer than the other in order to target delivery of therapeutic at the ends of the stent, to help prevent restenosis at the ends of the stent.

With regard to the coatings discussed above, the term "therapeutic agent" as used herein includes one or more "therapeutic agents" or "drugs." The terms "therapeutic agents" and "drugs" are used interchangeably herein.

The therapeutic agent may be any pharmaceutically acceptable agent such as a non-genetic therapeutic agent, a biomolecule, a small molecule, or cells.

Exemplary non-genetic therapeutic agents include anti-thrombogenic agents such heparin, heparin derivatives, prostaglandin (including micellar prostaglandin E1), urokinase, and PPack (dextrophenylalanine proline arginine chloromethylketone); anti-proliferative agents such as enoxaprin, angiopeptin, sirolimus (rapamycin), tacrolimus, everolimus, monoclonal antibodies capable of blocking smooth muscle cell proliferation, hirudin, and acetylsalicylic acid; anti-inflammatory agents such as dexamethasone, rosiglitazone, prednisolone, corticosterone, budesonide, estrogen, estradiol, sulfasalazine, acetylsalicylic acid, mycophenolic acid, and mesalamine; anti-neoplastic/anti-proliferative/anti-mitotic agents such as paclitaxel, cladribine, 5-fluorouracil, methotrexate, doxorubicin, daunorubicin, cyclosporine, cisplatin, vinbiastine, vincristine, epothilones, endostatin, trapidil, and angiostatin; anti-cancer agents such as antisense inhibitors of c-myc oncogene; anti-microbial agents such as triclosan, cephalosporins, aminoglycosides, nitrofurantoin, silver ions, compounds, or salts; biofilm synthesis inhibitors such as non-steroidal anti-inflammatory agents and chelating agents such as ethylenediaminetetraacetic acid, O,O'-bis (2-aminoethyl)ethyleneglycol-N,N, N',N'-tetraacetic acid and mixtures thereof; antibiotics such as gentamycin, rifampin, minocyclin, and ciprofolxacin; antibodies including chimeric antibodies and antibody fragments; anesthetic agents such as lidocaine, bupivacaine, and ropivacaine; nitric oxide; nitric oxide (NO) donors such as linsidomine, molsidomine, L-arginine, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warfarin sodium, Dicumarol, aspirin, prostaglandin inhibitors, platelet inhibitors and tick antiplatelet factors; vascular cell growth promoters such as growth factors, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; and any combinations and prodrugs of the above.

Exemplary biomolecules include peptides, polypeptides and proteins; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include monocyte chemoattractant proteins ("MCP-1) and bone morphogenic proteins ("BMP's"), such as, for example, BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15. Preferred BMPS are any of BMP-2, BMP-3, BMP-4, BMP-5, BMP-6, and BMP-7. These BMPs can be provided homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them. Non-limiting examples of genes include survival genes that protect against cell death, such as anti-apoptotic Bcl-2 family factors and Akt kinase and combinations thereof. Non-limiting examples of angiogenic factors include acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor, and insulin like growth factor. A non-limiting example of a cell cycle inhibitor is a cathepsin D (CD) inhibitor. Non-limiting examples of anti-restenosis agents include p15, p16, p18, p19, p21, p27, p53, p57, Rb, nFkB and E2F decoys, thymidine kinase ("TK") and combinations thereof and other agents useful for interfering with cell proliferation.

Exemplary small molecules include hormones, nucleotides, amino acids, sugars, and lipids and compounds have a molecular weight of less than 100 kD.

Exemplary cells include stem cells, progenitor cells, endothelial cells, adult cardiomyocytes, and smooth muscle cells. Cells can be of human origin (autologous or allogenic) or from an animal source (xenogenic), or genetically engineered.

Any of the therapeutic agents may be combined to the extent such combination is biologically compatible.

Any of the above mentioned therapeutic agents may be incorporated into a polymeric coating on the medical device or applied onto a polymeric coating on a medical device. With respect to the type of polymers that may be used in the coating according to the present invention, such polymers may be biodegradable or non-biodegradable. Non-limiting examples of suitable non-biodegradable polymers include polyvinylpyrrolidone including cross-linked polyvinylpyrrolidone; polyvinyl alcohols, copolymers of vinyl monomers such as EVA; polyvinyl ethers; polyvinyl aromatics; polyethylene oxides; polyesters including polyethylene terephthalate; polyamides; polyacrylamides; polyethers including polyether sulfone; polyalkylenes including polypropylene, polyethylene and high molecular weight polyethylene; polyurethanes; polycarbonates, silicones; siloxane polymers; polymer dispersions such as polyurethane dispersions (BAYHDROL®); squalene emulsions; and mixtures and copolymers of any of the foregoing.

Non-limiting examples of suitable biodegradable polymers include polycarboxylic acid, polyanhydrides including maleic anhydride polymers; polyorthoesters; poly-amino acids; polyethylene oxide; polyphosphazenes; polylactic acid, polyglycolic acid and copolymers and mixtures thereof such as poly(L-lactic acid) (PLLA), poly(D,L,-lactide), poly (lactic acid-co-glycolic acid), 50/50 (DL-lactide-co-glycolide); polydioxanone; polypropylene fumarate; polydepsipeptides; polycaprolactone and co-polymers and mixtures thereof such as poly(D,L-lactide-co-caprolactone) and polycaprolactone co-butylacrylate; polyhydroxybutyrate valerate and blends; polycarbonates such as tyrosine-derived polycarbonates and arylates, polyiminocarbonates, and polydimethyltrimethylcarbonates; cyanoacrylate; calcium phosphates; polyglycosaminoglycans; macromolecules such as polysaccharides (including hyaluronic acid; cellulosic polymers such as cellulose, cellulose acetate, and hydroxypropylmethyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), polyorthoesters, maleic anhydride copolymers, and zinc-calcium phosphate.

In a preferred embodiment, the polymer is polyacrylic acid available as HYDROPLUS° (Boston Scientific Corporation, Natick, Mass.), and described in U.S. Pat. No. 5,091,205, the disclosure of which is incorporated by reference herein. In a more preferred embodiment, the polymer is a co-polymer of polylactic acid and polycaprolactone.

Such coatings used with the present invention may be formed by any method known to one in the art. For example, an initial polymer/solvent mixture can be formed and then the therapeutic agent added to the polymer/solvent mixture. Alternatively, the polymer, solvent, and therapeutic agent can be added simultaneously to form the mixture. The polymer/solvent mixture may be a dispersion, suspension or a solution. The therapeutic agent may also be mixed with the polymer in the absence of a solvent. The therapeutic agent may be dissolved in the polymer/solvent mixture or in the polymer to be in a true solution with the mixture or polymer, dispersed into fine or micronized particles in the mixture or polymer, suspended in the mixture or polymer based on its solubility profile, or combined with micelle-forming compounds such as surfactants or adsorbed onto small carrier particles to create a suspension in the mixture or polymer. The coating may comprise multiple polymers and/or multiple therapeutic agents.

The coating can be applied to the medical device by any known method in the art including dipping, spraying, rolling, brushing, electrostatic plating or spinning, vapor deposition, air spraying including atomized spray coating, and spray coating using an ultrasonic nozzle.

The coating is typically from about 1 to about 50 microns thick. In the case of balloon catheters, the thickness is preferably from about 1 to about 10 microns, and more preferably from about 2 to about 5 microns. Very thin polymer coatings, such as about 0.2-0.3 microns and much thicker coatings, such as more than 10 microns, are also possible. It is also within the scope of the present invention to apply multiple layers of polymer coatings onto the medical device. Such multiple layers may contain the same or different therapeutic agents and/or the same or different polymers. Methods of choosing the type, thickness and other properties of the polymer and/or therapeutic agent to create different release kinetics are well known to one in the art.

The medical device may also contain a radio-opacifying agent within its structure to facilitate viewing the medical device during insertion and at any point while the device is implanted. Non-limiting examples of radio-opacifying agents are bismuth subcarbonate, bismuth oxychloride, bismuth trioxide, barium sulfate, tungsten, and mixtures thereof.

While the present invention has been described with reference to what are presently considered to be preferred embodiments thereof, it is to be understood that the present invention is not limited to the disclosed embodiments or constructions. On the contrary, the present invention is intended to cover various modifications and equivalent arrangements. In addition, while the various elements of the disclosed invention are described and/or shown in various combinations and configurations, which are exemplary, other combinations and configurations, including more, less or only a single embodiment, are also within the spirit and scope of the present invention.

What is claimed is:

1. A stent assembly for insertion into a lumen of a patient, comprising:
   a first metallic stent that provides internal scaffolding support for the lumen to resist radial compression and having a plurality of struts forming a patterned structure;
   a second metallic stent that provides internal scaffolding support for the lumen to resist radial compression and having a plurality of struts forming a patterned structure; and a delivery device adapted to expand the stents simultaneously;
   wherein the first stent is located inside of the second stent, and the stents are affixed to each other prior to insertion into the patient;
   wherein each of the first stent and the second stent has a therapeutic coating on it; and
   wherein the therapeutic coating on the first stent differs from the therapeutic coating on the second stent.

2. The stent assembly of claim 1, wherein the patterned structure of the first stent is generally the same as the patterned structure of the second stent.

3. The stent assembly of claim 1, wherein the patterned structure of the first stent is different from the patterned structure of the second stent.

4. A preassembled stent assembly for insertion into a lumen of a patient, comprising:
   a first stent that provides internal scaffolding support for the lumen to resist radial compression;
   a second stent that provides internal scaffolding support for the lumen to resist radial compression;
   a delivery device adapted to expand the stents simultaneously;
   wherein the first stent is located at least substantially inside of the second stent prior to insertion into the patient, and each of the stents has a therapeutic coating on it; and
   wherein the therapeutic coating on the first stent differs from the coating on the second stent.

5. The stent assembly of claim 4, wherein the first stent is affixed to the second stent.

6. The stent assembly of claim 4, wherein each of the first stent and the second stent has a patterned structure, and the patterned structure of the first stent is generally the same as the patterned structure of the second stent.

7. The stent assembly of claim 4, wherein each of the first stent and the second stent has a patterned structure, and the patterned structure of the first stent is different from the patterned structure of the second stent.

8. The stent assembly of claim 4, wherein the first stent has a different length from the second stent.

* * * * *